(12) United States Patent
Iijima

(10) Patent No.: US 9,266,805 B2
(45) Date of Patent: Feb. 23, 2016

(54) SYSTEM AND METHOD FOR PRODUCING GASOLINE OR DIMETHYL ETHER

(71) Applicant: MITSUBISHI HEAVY INDUSTRIES, LTD., Tokyo (JP)

(72) Inventor: Masaki Iijima, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/361,184

(22) PCT Filed: Nov. 26, 2012

(86) PCT No.: PCT/JP2012/080435
§ 371 (c)(1),
(2) Date: May 28, 2014

(87) PCT Pub. No.: WO2013/080906
PCT Pub. Date: Jun. 6, 2013

(65) Prior Publication Data
US 2014/0336420 A1    Nov. 13, 2014

(30) Foreign Application Priority Data

Nov. 30, 2011   (JP) .................................. 2011-261759

(51) Int. Cl.
*C07C 41/09*     (2006.01)
*C10G 3/00*      (2006.01)
(Continued)

(52) U.S. Cl.
CPC .................. *C07C 41/09* (2013.01); *C01B 3/382* (2013.01); *C07C 29/1518* (2013.01); *C10G 3/00* (2013.01);
(Continued)

(58) Field of Classification Search
CPC combination set(s) only.
See application file for complete search history.

(56) References Cited

U.S. PATENT DOCUMENTS 4,048,250 A * 9/1977 Garwood et al. ............. 518/704
4,282,187 A   8/1981 Corbett et al.
(Continued)

FOREIGN PATENT DOCUMENTS

EA       004130 B1   12/2003
EP     1 180 495 A2    2/2002
(Continued)

OTHER PUBLICATIONS

Russian Office Action dated Mar. 11, 2015, issued in corresponding RU Patent Application No. 2014121982 with English translation (6 pages).
(Continued)

*Primary Examiner* — Lessanework Seifu
(74) *Attorney, Agent, or Firm* — Westerman, Hattori, Daniels & Adrian, LLP

(57) ABSTRACT

A system or method for producing gasoline or dimethyl ether from natural gas via methanol includes: steam-reforming natural gas to generate reformed gas; synthesizing methanol from the reformed gas; synthesizing gasoline or dimethyl ether from the methanol; and at least one is selected from the group consisting of: pre-reforming natural gas prior to the steam-reforming; recovering carbon dioxide from flue gas generated in the steam-reforming; and preheating combustion air to be supplied to the steam-reforming by using synthesis heat generated in the synthesis of gasoline or dimethyl ether. In addition, an overall energy balance of the system is constructed by using heat recovery from flue gas generated in the steam-reforming, heat recovery from the reformed gas, synthesis heat generated in the synthesis of methanol, synthesis heat generated in the synthesis of gasoline or DME, and heat recovered in the pre-reforming, carbon dioxide recovering, or air preheating, respectively if selected.

7 Claims, 4 Drawing Sheets

(51) Int. Cl.
  *C10L 1/06* (2006.01)
  *C07C 29/151* (2006.01)
  *C01B 3/38* (2006.01)

(52) U.S. Cl.
  CPC ... *C10G 3/42* (2013.01); *C10L 1/06* (2013.01); *C01B 2203/0233* (2013.01); *C01B 2203/061* (2013.01); *C01B 2203/0811* (2013.01); *C01B 2203/1058* (2013.01); *C01B 2203/1241* (2013.01); *C01B 2203/142* (2013.01); *C10G 3/49* (2013.01); *C10G 2400/02* (2013.01)

(56) References Cited

U.S. PATENT DOCUMENTS

| | | | |
|---|---|---|---|
| 4,523,046 | A | 6/1985 | Gould et al. |
| 5,177,114 | A | 1/1993 | Van Dijk et al. |
| 6,218,439 | B1 | 4/2001 | Kobayashi et al. |
| 2002/0165417 | A1 | 11/2002 | Numaguchi et al. |
| 2013/0109888 | A1* | 5/2013 | Moon et al. ............... 568/671 |

FOREIGN PATENT DOCUMENTS

| | | |
|---|---|---|
| JP | 04-51596 B2 | 8/1992 |
| JP | 2001-097906 A | 4/2001 |
| JP | 2002-338206 A | 11/2002 |
| RU | 2126376 C1 | 2/1999 |
| RU | 2204527 C2 | 5/2003 |

OTHER PUBLICATIONS

Notification of Transmittal of Translation of the International Preliminary Report on Patentability (Form PCT/IB/338) of International Application No. PCT/JP2012/080435 mailing date of Jun. 12, 2014, with Forms PCT/IB/373 and PCT/ISA/237.
Concise Explanation of the Relevance of Honda, Yasuhiro, "The GTG(Gas-To-Gasoline) Project just launched in New Zealand", Petrotech, Nov. 1, 1986, vol. 9, No. 11, pp. 986-991.
International Search Report, dated Feb. 5, 2013, issued in corresponding application No. PCT/JP2012/080435.
Honda, Yasuhiro, "The GTG (Gas-To-Gasoline) Project just launched in New Zealand", Petrotech, Nov. 1, 1986, vol. 9, No. 11, pp. 986-991.
Gonzalez et al., "Process comparison biomass-to-liquid (BtL) routes Fischer-Tropsch synthesis and methanol to gasoline", Biomass Conversion and Biorefinery, Oct. 2, 2011, pp. 229-243, vol. 1, No. 4; cited in European Search Report dated Jul. 1, 2015.
European Search Report dated Jul. 1, 2015, issued in counterpart application No. 12854279.2 (9 pages).
Notice of Allowance dated Oct. 13, 2015, issued in counterpart Russian Patent application No. 2014121982 with Concise Explanation of Relevance (13 pages).

* cited by examiner

SYSTEM AND METHOD FOR PRODUCING GASOLINE OR DIMETHYL ETHER

TECHNICAL FIELD

The present invention relates to a system to and a method for producing gasoline or dimethyl ether, and more specifically relates to a system to and a method for producing gasoline or dimethyl ether from natural gas via methanol.

BACKGROUND ART

In synthesizing methanol from natural gas, in most cases, natural gas is steam-reformed, then reformed gas containing hydrogen and carbon monoxide is generated, and methanol is then synthesized from the reformed gas. In a synthetic plant for producing methanol in the above-described manner, steam and heat required within the plant are provided by heat recovery from flue gas generated by the steam reforming and heat recovery from reformed gas and also by using heat of reaction resulting from the synthesis of methanol so that the so-called self-balance is secured at the stage of designing of the system.

On the other hand, Japanese Patent Publication (B2) No. H04-51596 discloses a method for synthesizing gasoline from methanol via dimethyl ether (DME). A reaction for synthesizing DME from methanol is an exothermic reaction, and the heat of reaction is 231 kcal equivalent to 1 kg of methanol. In addition, a reaction for synthesizing gasoline from methanol via DME is also an exothermic reaction, and the heat of reaction is 416 kcal equivalent to 1 kg of methanol.

BACKGROUND LITERATURE

Patent Literature

Patent Literature 1: Japanese Patent Publication (B2) No. H04-51596

DISCLOSURE OF INVENTION

Problem to be Solved by Invention

In producing DME or gasoline from natural gas in a methanol synthesis plant in which a synthesis column for synthesizing DME or gasoline from methanol as discussed in Japanese Patent Publication (B2) No. H04-51596 is installed, energy becomes excessive compared with the self-balance of energy secured in a conventional methanol synthesis plants because the reaction for synthesizing DME or gasoline is an exothermic reaction, as described above. However, a problem may arise in that exothermic energy generated by a reaction for synthesizing DME or gasoline may be of no use within the plant and therefore will be wasted.

Further, in methanol synthesis plants, a distillation operation for removing moisture from methanol is performed in the production process, but the heat used for distillation may be in excess because a distillation operation like this is not necessary for synthesizing DME and gasoline from methanol.

In order to solve the above-described problem, the purpose of the invention is to provide a system or a method for producing gasoline or DME from natural gas via methanol, which is capable, in producing gasoline or DME from natural gas via methanol, of effectively using exothermic energy generated by the synthesis of gasoline or DME and heat generated and remaining because distillation of methanol is unnecessary without having to waste it.

Means for Solving the Problem

In an aspect, the present invention provides a system for producing gasoline or DME from natural gas via methanol includes: a steam-reforming device for steam-reforming natural gas to generate reformed gas; a methanol synthesis device for synthesizing methanol from the reformed gas generated by the steam reforming device; a gasoline or DME synthesis device for synthesizing gasoline or DME from the methanol synthesized by the methanol synthesis device; and at least one device selected from the group consisting of: a pre-reforming device for pre-reforming the natural gas prior to the steam-reforming of the natural gas; a carbon dioxide recovery device for recovering carbon dioxide from flue gas of the steam reforming device; and an air preheating device for preheating combustion air to be supplied to the steam-reforming device by using the gasoline or DME synthesis device, wherein an overall energy balance of the system is constructed by using heat recovery from the flue gas generated in the steam-reforming device, heat recovery from the reformed gas, synthesis heat generated in the methanol synthesis device, synthesis heat generated in the gasoline or dimethyl ether synthesis device, heat recovered in the pre-reforming device if selected, heat recovered in the carbon dioxide recovery device during recovery of carbon dioxide if selected, and heat recovered in the air preheat device if selected.

In another aspect, the present invention provides a method for producing gasoline or DME from natural gas via methanol includes: a steam-reforming step of steam-reforming natural gas to generate reformed gas; a methanol synthesis step of synthesizing methanol from the reformed gas generated in the steam-reforming step; a gasoline or DME synthesis step of synthesizing gasoline or DME from the methanol synthesized in the methanol synthesis step; and at least one step selected from the group consisting of: a pre-reforming step of pre-reforming the natural gas prior to the steam-reforming of the natural gas; a carbon dioxide recovery step of recovering carbon dioxide from flue gas of the steam-reforming step; and an air preheating step of preheating combustion air to be supplied to the steam-reforming step by using synthesis heat generated in the synthesis of gasoline or DME, wherein an overall energy balance of a system for carrying out the method is constructed by using heat recovery from the flue gas generated in the steam-reforming step, heat recovery from the reformed gas, synthesis heat generated in the methanol synthesis step, synthesis heat generated in the gasoline or dimethyl ether synthesis step, heat recovered in the pre-reforming step if selected, heat recovered in the carbon dioxide recovery step during recovery of carbon dioxide if selected, and heat recovered in the air preheating step if selected.

Advantageous Effects of Invention

As described above, according to the present invention, at least one is selected from the group consisting of: the pre-reforming for pre-reforming natural gas prior to the steam-reforming of natural gas; the carbon dioxide recovering for recovering carbon dioxide from flue gas generated in the steam-reforming; and the air preheating for preheating combustion air to be supplied to the steam-reforming by using synthesis heat generated in the synthesis of gasoline or DME, and in addition, an overall energy balance of the system is constructed by using heat recovery from flue gas generated in the steam-reforming, heat recovery from the reformed gas, synthesis heat generated in the synthesis of methanol, synthesis heat generated in the synthesis of gasoline or DME, and the heat recovered in the pre-reforming, carbon dioxide recovering, or air preheating, respectively, if selected, and thereby the exothermic energy generated in the synthesis of gasoline or DME can be effectively used without wasting it.

DESCRIPTION OF EMBODIMENTS

Hereinbelow, an embodiment of a system and a method for producing gasoline from natural gas via methanol according to the present invention will be described with reference to the accompanying drawings.

Figure 1:
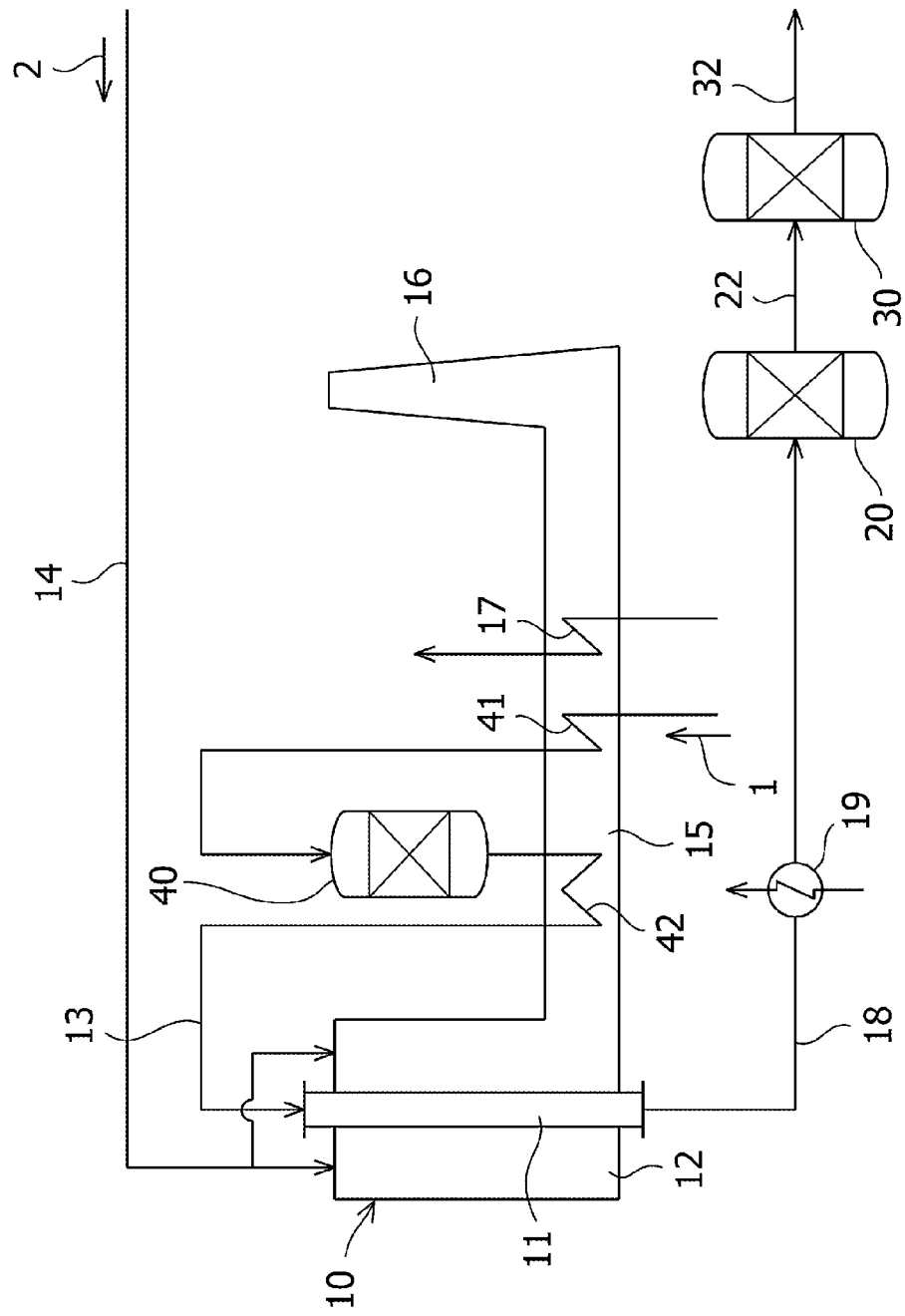
FIG. 1 is a schematic view showing an embodiment of a system for producing gasoline from natural gas via methanol according to the present invention.

As shown in FIG. 1, the system according to the present embodiment mainly includes a steam reformer 10, which is configured to generate reformed gas by steam-reforming natural gas, a methanol synthesis column 20, which is configured to synthesize methanol from the reformed gas generated by the steam reformer, a gasoline synthesis column 30, which is configured to synthesize gasoline from the methanol synthesized by the methanol synthesis column, and a pre-reformer 40, which is configured to pre-reform natural gas before the natural gas is steam-reformed.

The steam reformer 10 primarily includes a reaction tube 11 for steam reforming, a burning portion 12 disposed around the reaction tube 11, a waste heat recovery portion 15, which is configured to recover waste heat of the flue gas generated in the burning portion 12, and a stack 16, which is configured to release the flue gas to the atmosphere after waste heat has been recovered therefrom. The reaction tube 11, which includes a steam reforming catalyst charged inside the tube, is a device for generating hydrogen, carbon monoxide, and carbon dioxide from natural gas containing methane as its main ingredient by carrying out the following reactions. For the steam reforming catalyst, known catalysts such as a nickel-based catalyst can be used, for example.

$$CH_4 + H_2O \rightarrow 3H_2 + CO \qquad (1)$$

$$CO + H_2O \rightarrow H_2 + CO_2 \qquad (2)$$

A material supply line 13 for supplying a material 1, which includes natural gas and steam, is connected to an inlet of the reaction tube 11. The burning portion 12 includes a combustion burner (not shown) for heating the reaction tube 11, and a fuel supply line 14 for supplying a fuel 2 such as natural gas is connected to the combustion burner. A reformed gas supply line 18 is connected to an outlet of the reaction tube 11, which is a line for supplying reformed gas containing hydrogen, carbon monoxide, and carbon dioxide generated by the steam reforming reaction as its main ingredients to a methanol synthesis column 20.

A pre-reformer 40 is a device configured to pre-reform C2 or higher hydrocarbons contained in the natural gas such as ethane, primarily, into C1 hydrocarbons such as methane, carbon monoxide, or hydrogen. The pre-reformer 40 includes a pre-reforming catalyst charged inside the tube. For the pre-reforming catalyst, known catalysts such as a nickel-based catalyst can be used.

The pre-reformer 40 is disposed on the upstream side of the steam reformer 10 in the direction of supply of the material, more specifically, in the material supply line 13. In the material supply line 13, a first flue gas-material heat exchanger 41, which is configured to preheat the material 1 with flue gas from the waste heat recovery portion 15, is provided on the further upstream side of the pre-reformer 40 in the direction of supply of the material, and a second flue gas-material heat exchanger 42, which is configured to preheat the material that has been pre-reformed by the pre-reformer 40 with the flue gas from the waste heat recovery portion 15, is provided on the downstream side of the pre-reformer 40 in the direction of supply of the material.

In other words, the waste heat recovery portion 15 of the steam reformer 10 includes the second flue gas-material heat exchanger 42 and the first flue gas-material heat exchanger 41 described above, and also a flue gas-steam heat exchanger 17, disposed in order of the flow of the flue gas from the burning portion 12 to the stack 16. The flue gas-steam heat exchanger 17 is a device for obtaining steam or heat to be used within the system, and is configured to recover heat from the flue gas and obtain high-pressure steam by heating boiler water and the like with the flue gas flowing inside the waste heat recovery portion 15.

Similarly, the reformed gas supply line 18 is provided with a reformed gas-steam heat exchanger 19, which is provided in order to obtain steam or heat to be used within the system. The reformed gas-steam heat exchanger 19 is a device configured to obtain high-pressure steam and recover heat from the reformed gas by heating boiler water and the like by using the reformed gas.

The methanol synthesis column 20 is a device configured to synthesize methanol from reformed gas by running the following reactions.

$$CO + 2H_2 \rightarrow CH_3OH \qquad (3)$$

$$CO_2 + 3H_2 \rightarrow CH_3OH + H_2O \qquad (4)$$

The methanol synthesis column 20 includes a methanol synthesis catalyst charged inside the tube. For the methanol synthesis catalyst, known catalysts such as a copper-based catalyst can be used. A methanol supply line 22 is connected to methanol synthesis column 20, which is a line for supplying methanol synthesized by the methanol synthesis column 20 to the gasoline synthesis column 30. Note that in addition to the synthesized methanol, liquid crude methanol containing water, which is a byproduct of the reaction of Formula 4, flows in the methanol supply line 22.

The gasoline synthesis column 30 is a device which is configured to synthesize gasoline from methanol by running the reactions of the following Formulae.

$$2CH_3OH \rightarrow CH_3OCH_3 + H_2O \qquad (5)$$

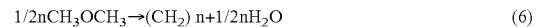

$$1/2n\,CH_3OCH_3 \rightarrow (CH_2)_n + 1/2nH_2O \qquad (6)$$

As described above, methanol is synthesized by the gasoline synthesis reaction expressed in Formula 3 into gasoline via the dimethyl ether (i.e., DME) synthesis reaction expressed by Formula 5. In the gasoline synthesis column 30, two types of catalysts including the DME synthesis catalyst and the gasoline synthesis catalyst are provided in two stages so that two reactions can be run in stages. For the DME synthesis catalyst, known catalysts such as an aluminosilicate type zeolite-based catalyst can be used, for example. In addition, for the gasoline synthesis catalyst, known catalysts such as an aluminosilicate type zeolite-based catalyst can be used.

A gasoline supply line 32 is connected with the gasoline synthesis column 30, which is a line for supplying gasoline synthesized by the gasoline synthesis column 30 to storage facilities (not shown). Note that although the example illustrated in FIG. 1 includes the gasoline synthesis column 30, a DME synthesis column, which is configured to produce DME by running the reactions up to the DME synthesis reaction of Formula 5, can be provided instead of the gasoline synthesis column 30.

According to the above-described configuration, the fuel 2 such as natural gas is first supplied to the burning portion 12 of the steam reformer 10 via the fuel supply line 14. In the burning portion 12, the fuel 2 is burned together with air, and the reaction tube 11 is heated to a temperature ranging from about 800° C. to about 900° C. The flue gas containing carbon dioxide generated in the burning portion 12 flows into the waste heat recovery portion 15.

On the other hand, the material 1 containing natural gas and steam is heated by the first flue gas-material heat exchanger 41 of the waste heat recovery portion 15 of the steam reformer 10 to a temperature ranging from about 450° C. to about 550° C., and then the heated material 1 is supplied to the pre-reformer 40. In the pre-reformer 40, C2 or higher hydrocarbons contained in the material 1, such as ethane, is pre-reformed into methane and the like. The pre-reformed gas is heated by the second flue gas-material heat exchanger 42 again to a temperature ranging from about 600° C. to about 700° C., and then it is supplied to the reaction tube 11 of the steam reformer 10 via the material supply line 13.

After the material 1 is heated serially by the second flue gas-material heat exchanger 42 and the first flue gas-material heat exchanger 41 of the waste heat recovery portion 15 as described above and heat is recovered by the flue gas-steam heat exchanger 17 by heating boiler water or the like, the flue gas containing carbon dioxide generated in the burning portion 12, which has the temperature of about 1,000° C., is released from the stack 16 to the atmosphere.

In the reaction tube 11 of the steam reformer 10, the material 1 is steam-reformed by the reactions of Formulae 1 and 2 and converted into reformed gas containing hydrogen, carbon monoxide, and carbon dioxide as its main ingredients. Before the reformed gas is supplied to the methanol synthesis column 20 via the reformed gas supply line 18, heat is recovered by the reformed gas-steam heat exchanger 19 by heating boiler water or the like.

In the methanol synthesis column 20, methanol is synthesized from the reformed gas by the reactions of Formulae 3 and 4. The methanol synthesis reactions are exothermic reactions. The temperature of the reformed gas is controlled by the reformed gas-steam heat exchanger 19 to the range of about 160° C. to about 200° C., which is suitable for synthesis of methanol. Methanol synthesized by the methanol synthesis column 20 is supplied to the gasoline synthesis column 30 via the methanol supply line 22 as crude methanol containing water.

In the gasoline synthesis column 30, gasoline is synthesized from methanol by the reactions of Formulae 5 and 6. The gasoline synthesis reactions are an exothermic reaction. In addition, because water is generated as a byproduct in the reaction of Formula 6, the crude methanol may contain water, and it is therefore not necessary to provide the methanol supply line 22 for supplying methanol to the gasoline synthesis column 30 with a purification device for removing water by distilling crude methanol, which is necessary in a conventional methanol synthesis plant.

In the present embodiment, as described above, and differently from conventional methanol synthesis plants, the gasoline synthesis column 30 is provided in which exothermic reactions are run and thermal energy is generated, and in addition, it becomes unnecessary to provide a methanol distillation column which consumes energy, and thereby the amount of supply of the fuel 2 to the burning portion 12 of the steam reformer 10 can be reduced, although excessive energy is generated, by providing the pre-reformer 40 to heat the material at locations across the pre-reformer 40 by using the first and the second flue gas-material heat exchangers 41 and 42 of the waste heat recovery portion 15 of the steam reformer 10. In addition, in the waste heat recovery portion 15 of the steam reformer 10, the recovered heat decreases because the first and the second flue gas-material heat exchangers 41 and 42 are provided; however, the system can be designed so that the energy of the entire system can be self-balanced by using the exothermic energy generated in the gasoline synthesis column 30 to compensate for the decreased heat.

Next, an embodiment illustrated in FIG. 2 will be described. A system of the present embodiment primarily includes the steam reformer 10, the methanol synthesis column 20, the gasoline synthesis column 30, and a $CO_2$ recovery device 50, which is configured to remove $CO_2$ from flue gas of the steam reformer. Note that the same configurations as those of the system illustrated in FIG. 1 are provided with the same reference symbols, and detailed descriptions thereof will not be repeated here.

The $CO_2$ recovery device 50 is a device configured to absorb and remove carbon dioxide from flue gas by bringing $CO_2$ absorbing liquid into gas-liquid contact with the flue gas that flows in the waste heat recovery portion 15 of the steam reformer 10. The $CO_2$ recovery device 50 is disposed on the flue gas downstream side of the flue gas-steam heat exchanger 17. Note that an absorbing liquid regeneration device (not shown) is added to the $CO_2$ recovery device 50. The absorbing liquid regeneration device is a device configured to obtain carbon dioxide gas as well as regenerate the $CO_2$ absorbing liquid by separating carbon dioxide from the $CO_2$ absorbing liquid which has absorbed carbon dioxide.

The $CO_2$ recovery device 50 is provided with a $CO_2$ supply line 51 for supplying the recovered carbon dioxide gas to the methanol synthesis column 20 to reuse it as a material of the reaction expressed by Formula 4 mentioned above, which is run in the methanol synthesis column 20.

With the above-described configuration, first, the fuel 2 such as natural gas is supplied to the burning portion 12 of the steam reformer 10 via the fuel supply line 14. In the burning portion 12, the fuel 2 is burned together with air, and the reaction tube 11 is heated to a temperature ranging from about 800° C. to about 900° C. After boiler water or the like is heated by the flue gas-steam heat exchanger 17 of the waste heat recovery portion 15 to recover heat and $CO_2$ is removed by the $CO_2$ recovery device 50, the flue gas containing carbon dioxide generated in the burning portion 12, which has the temperature of about 1,000° C., is released from the stack 16 to the atmosphere.

On the other hand, the material 1 containing natural gas and steam is supplied to the reaction tube 11 of the steam reformer 10 via the material supply line 13. In the reaction tube 11 of the steam reformer 10, the material 1 is converted by a steam reforming reaction into reformed gas. After heat is recovered by heating boiled water or the like by the reformed gas-steam heat exchanger 19, the reformed gas is supplied to the methanol synthesis column 20 via the reformed gas feed line 18. In addition, carbon dioxide recovered by the $CO_2$ recovery device 50 is also supplied to the methanol synthesis column 20 via the $CO_2$ supply line 51.

In the methanol synthesis column 20, methanol is synthesized from the reformed gas and the carbon dioxide gas by running the reactions of Formulae 3 and 4. By adding the carbon dioxide gas, excessive hydrogen contained in the reformed gas can be converted into methanol, and as a result, the production of methanol can be increased. In addition, because the methanol synthesis reactions are an exothermic reaction, the exothermic energy generated in the methanol synthesis column 20 increases as the production of methanol increases. Methanol synthesized by the methanol synthesis column 20 is supplied to the gasoline synthesis column 30 via the methanol supply line 22 as crude methanol containing water.

In the gasoline synthesis column 30, gasoline is synthesized from methanol by the reactions of Formulae 5 and 6. Because the supply of methanol increases, the production of gasoline also increases, and the exothermic energy generated in the gasoline synthesis column 30 also increases in accordance with the increase in the production because the gasoline synthesis reactions are an exothermic reaction.

In the present embodiment, as described above and differently from conventional methanol synthesis plants, the gasoline synthesis column 30 is provided in which exothermic reactions are run and thermal energy is generated, and in addition, it becomes unnecessary to provide a methanol distillation column which consumes energy, and thereby the system can be designed, although excessive energy is generated, so that the energy of the entire system can be self-balanced by providing the $CO_2$ recovery device 50 and the absorbing liquid regeneration device (not shown) that consume energy. In addition, the production of gasoline in the gasoline synthesis column 30 can be increased by supplying carbon dioxide recovered by the $CO_2$ recovery device 50 to the methanol synthesis column 20 together with the reformed gas.

An embodiment illustrated in FIG. 3 will be described. A system of the present embodiment primarily includes the steam reformer 10, the methanol synthesis column 20, the gasoline synthesis column 30, and an the air preheater 60, which is configured to preheat combustion air to be supplied to the burning portion of the steam reformer. Note that the same configurations as those of the system illustrated in FIGS. 1 and 2 are provided with the same reference symbols, and detailed descriptions thereof will not be repeated here.

The air preheater 60 includes a fan 63 for feeding combustion air, a flue gas-combustion air heat exchanger 62, which is configured to preheat combustion air with the flue gas that flows in the waste heat recovery portion 15 of the steam reformer 10, a combustion air introduction line 61 for introducing the preheated combustion air into the gasoline synthesis column 30 with the synthesis heat generated in the gasoline synthesis column 30 in order to further heat the preheated combustion air, and a combustion air supply line 64 for supplying the combustion air heated with the synthesis heat to the burning portion 12 of the steam reformer 10. The flue gas-combustion air heat exchanger 62 is disposed on the flue gas downstream side of the flue gas-steam heat exchanger 17.

Means for heating combustion air with the heat of reaction generated in the gasoline synthesis column 30 is not limited to specific means, but for example, the combustion air can be heated with steam obtained by heating boiler water with the heat of reaction generated in the gasoline synthesis column 30. Alternatively, heat can be exchanged between the DME synthesis catalyst in the gasoline synthesis column 30 or the reaction tube (not shown) charged with the gasoline synthesis catalyst and the combustion air.

According to the above-described configuration, the fuel 2 such as natural gas is first supplied to the burning portion 12 of the steam reformer 10 via the fuel supply line 14. In the burning portion 12, the fuel 2 is burned together with air, and the reaction tube 11 is heated to a temperature ranging from about 800° C. to about 900° C. After boiler water or the like is heated by the flue gas-steam heat exchanger 17 of the waste heat recovery portion 15 to recover heat and $CO_2$ is removed by the $CO_2$ recovery device 50, the flue gas containing carbon dioxide generated in the burning portion 12, which has the temperature of about 1,000° C., is cooled to a temperature ranging from about 300° C. to about 400° C. Then, after the combustion air from the fan 63 is heated by the flue gas-combustion air heat exchanger 62, the flue gas is released from the stack 16.

On the other hand, the material 1 containing natural gas and steam is supplied to the reaction tube 11 of the steam reformer 10 via the material supply line 13. In the reaction tube 11 of the steam reformer 10, the material 1 is converted into reformed gas by a steam reforming reaction. After heat is recovered by heating boiled water or the like by using the reformed gas-steam heat exchanger 19, the reformed gas is supplied to the methanol synthesis column 20 via the reformed gas feed line 18.

In the methanol synthesis column 20, methanol is synthesized from the reformed gas and carbon dioxide gas. Methanol synthesized by the methanol synthesis column 20 is supplied to the gasoline synthesis column 30 via the methanol supply line 22 as crude methanol containing water.

In the gasoline synthesis column 30, gasoline is synthesized from methanol by the reactions of Formulae 5 and 6. The synthesis reaction from methanol to DME run in the gasoline synthesis column 30 is an exothermic reaction, and its heat of reaction is 185 kcal equivalent to 1 kg of methanol. In addition, the gasoline synthesis reaction is also an exothermic reaction, and its heat of reaction is 231 kcal equivalent to 1 kg of methanol. Therefore, in synthesizing gasoline from methanol, the heat of reaction is 416 kcal equivalent to 1 kg of methanol. The combustion air introduced from the combustion air inlet line 61 is heated by using this heat of reaction.

With respect to the condition of the DME synthesis reaction performed by the gasoline synthesis column 30, it is preferable that the temperature range from 250° C. to 300° C. In addition, for the condition of the gasoline synthesis reaction, it is preferable that the temperature range from 380° C. to 450° C. Therefore, the combustion air can be heated up to the range of about 300° C. to about 380° C.

The combustion air heated by the gasoline synthesis column 30 is supplied to the burning portion 13 of the steam reformer 10 via the combustion air supply line 64 together with the fuel 2. Because the combustion air is heated as described above, the supply of the fuel 2 to the burning portion 13 can be reduced.

In the present embodiment, as described above and differently from conventional methanol synthesis plants, the gasoline synthesis column 30 is provided in which exothermic reactions are run and thermal energy is generated, and in addition, it becomes unnecessary to provide a methanol distillation column which consumes energy, and thereby the system can be designed, although excessive energy is generated, so that the energy of the entire system can be self-balanced because the supply of the fuel 2 to the steam reformer 10 can be reduced by preheating the combustion air in the steam reformer 10 and preheating the combustion air by using the exothermic energy generated in the gasoline synthesis column 30.

An embodiment illustrated in FIG. 4 will be described. A system of the present embodiment is a combination of all the embodiments illustrated in FIGS. 1 to 3. More specifically, the system primarily includes the steam reformer 10, the methanol synthesis column 20, the gasoline synthesis column 30, the pre-reformer 40, the $CO_2$ recovery device 50, and the air preheater 60, which is configured to preheat air to be supplied to the burning portion of the steam reformer. Note that the same configurations as those of the system illustrated in FIGS. 1 to 3 are provided with the same reference symbols, and detailed descriptions thereof will not be repeated here.

The components of the waste heat recovery portion 15 of the steam reformer 10 are disposed in the following order from the flue gas upstream side, i.e., the second flue gas-material heat exchanger 42, the first flue gas-material heat exchanger 41, the flue gas-steam heat exchanger 17, the flue gas-combustion air heat exchanger 62, and the $CO_2$ recovery device 50.

According to the above-described configuration, the fuel 2 such as natural gas is first supplied to the burning portion 12 of the steam reformer 10 via the fuel supply line 14. In the burning portion 12, the fuel 2 is burned together with air, and the reaction tube 11 is heated to a temperature ranging from about 800° C. to about 900° C. After the material is heated by the second flue gas-material heat exchanger 42 and cooled to a temperature ranging from about 450° C. to about 550° C. and the material is heated by the first flue gas-material heat exchanger 41, the flue gas containing carbon dioxide generated in the burning portion 12, which has the temperature of about 1,000° C., is cooled to a temperature ranging from about 600° C. to about 700° C. Next, boiler water or the like is heated by the flue gas-steam heat exchanger 17 of the waste heat recovery portion 15, cooled to a temperature ranging from about 300° C. to about 400° C., and then heat is recovered by heating the combustion air by using the flue gas-combustion air heat exchanger 62. Then, after $CO_2$ is removed by the $CO_2$ recovery device 50, the flue gas is released from the stack 16 to the atmosphere.

On the other hand, the material 1 containing natural gas and steam is supplied to the reaction tube 11 of the steam reformer 10 via the material supply line 13. In the reaction tube 11 of the steam reformer 10, the material 1 is converted by a steam reforming reaction into reformed gas. After heat is recovered by heating boiled water or the like by using the reformed gas-steam heat exchanger 19, the reformed gas is supplied to the methanol synthesis column 20 via the reformed gas feed line 18. In addition, carbon dioxide recovered by the $CO_2$ recovery device 50 is also supplied to the methanol synthesis column 20 via the $CO_2$ supply line 51.

In the methanol synthesis column 20, methanol is synthesized from the reformed gas and carbon dioxide gas by running the reactions of Formulae 3 and 4. By adding the carbon dioxide gas, the production of the methanol and exothermic energy can be increased in the methanol synthesis column 20. Methanol synthesized by the methanol synthesis column 20 is supplied to the gasoline synthesis column 30 via the methanol supply line 22 as crude methanol containing water.

In the gasoline synthesis column 30, gasoline is synthesized from methanol by running the reactions of Formulae 5 and 6. Because the supply of methanol increases, the production of gasoline and the exothermic energy can be increased in the gasoline synthesis column 30. In the gasoline synthesis column 30, the combustion air introduced from combustion air inlet line 61 is heated by the heat of reaction.

In the present embodiment, as described above and differently from conventional methanol synthesis plants, the gasoline synthesis column 30 is provided in which exothermic reactions are run and thermal energy is generated, and in addition, it becomes unnecessary to provide a methanol distillation column which consumes energy, and thereby the amount of supply of the fuel 2 to the steam reformer 10 can be reduced, although excessive energy is generated, by providing the pre-reformer 40, the $CO_2$ recovery device 50 and the absorbing liquid regeneration device (not shown), and the air preheater 60 which preheats combustion air by using the heat of reaction of the gasoline synthesis column 30 and by heating the material at locations across the pre-reformer 40 by using the first and the second flue gas-material heat exchangers 41 and 42 of the waste heat recovery portion 15 of the steam reformer 10, and the supply of the fuel 2 to the steam reformer 10 can also be reduced by preheating the combustion air. In addition, in the waste heat recovery portion 15 of the steam reformer 10, the recovered heat decreases because the first and the second flue gas-material heat exchangers 41 and 42 are provided, however, the system can be designed so that the energy of the entire system can be self-balanced because the exothermic energy generated in the gasoline synthesis column 30 can be used to compensate for the decreased heat. The production of gasoline in the gasoline synthesis column 30 can be increased by supplying carbon dioxide recovered by the $CO_2$ recovery device 50 to the methanol synthesis column 20 together with the reformed gas. Further, the supply of the fuel 2 can be reduced by converting the entire carbon dioxide gas or a part thereof recovered by the $CO_2$ recovery device 50 into carbon monoxide gas and by supplying it to the burning portion 12 of the steam reformer 10 together with the fuel 2, which also enables self-balancing of the system.

EXAMPLES

Figure 2:
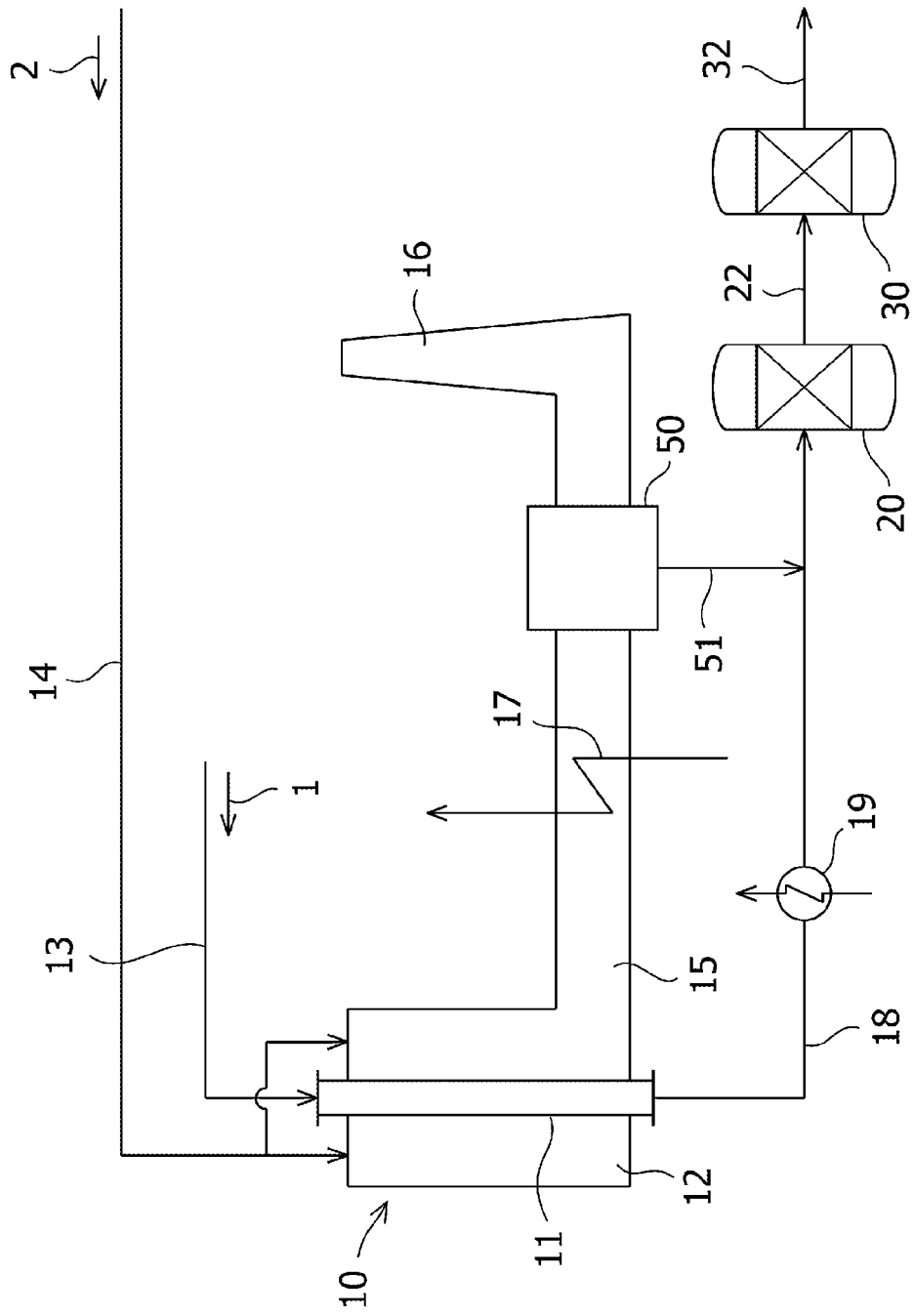
FIG. 2 is a schematic view showing another embodiment of a system for producing gasoline from natural gas via methanol according to the present invention.
Figure 3:
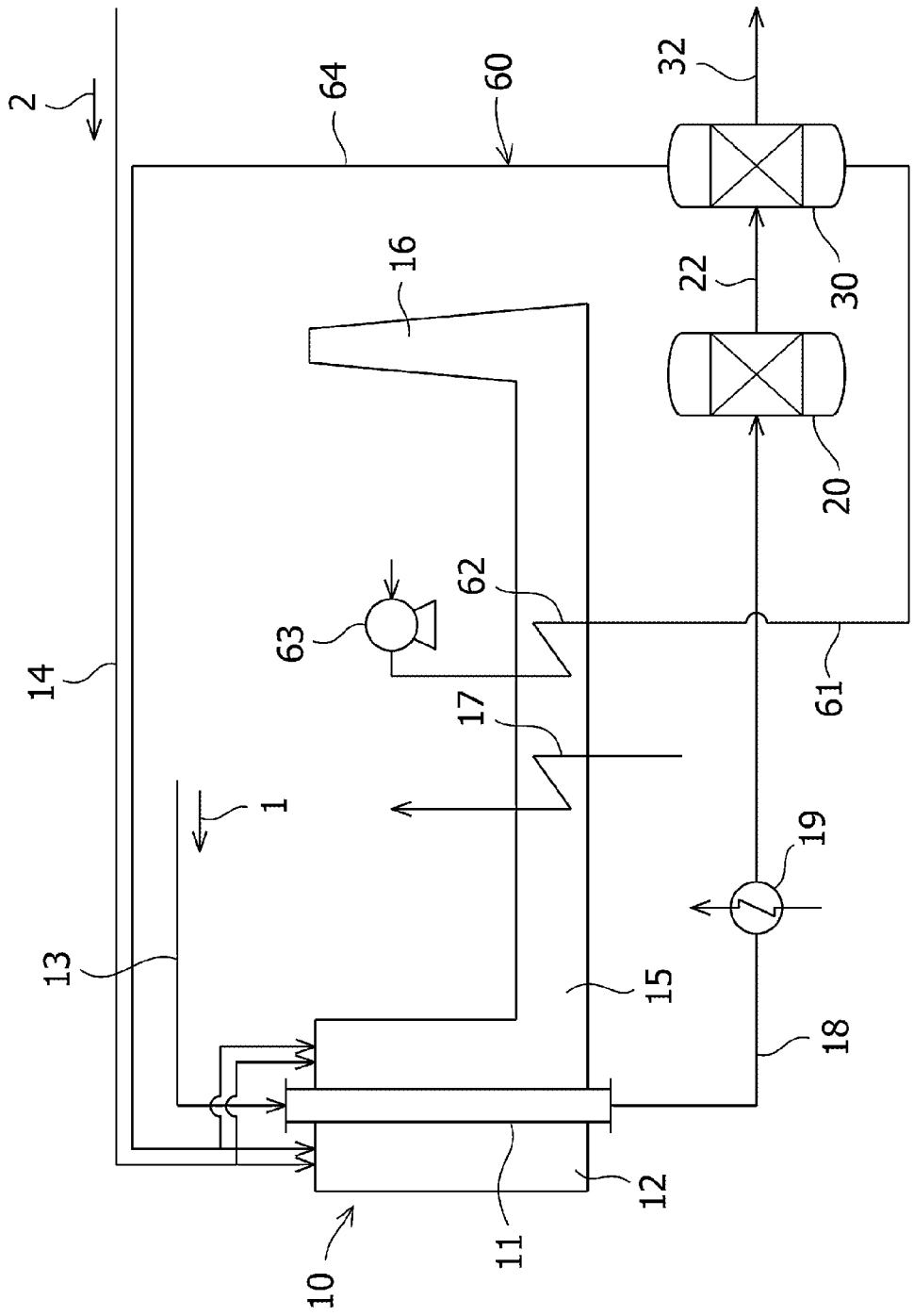
FIG. 3 is a schematic view showing still another embodiment of a system for producing gasoline from natural gas via methanol according to the present invention.
Figure 4:
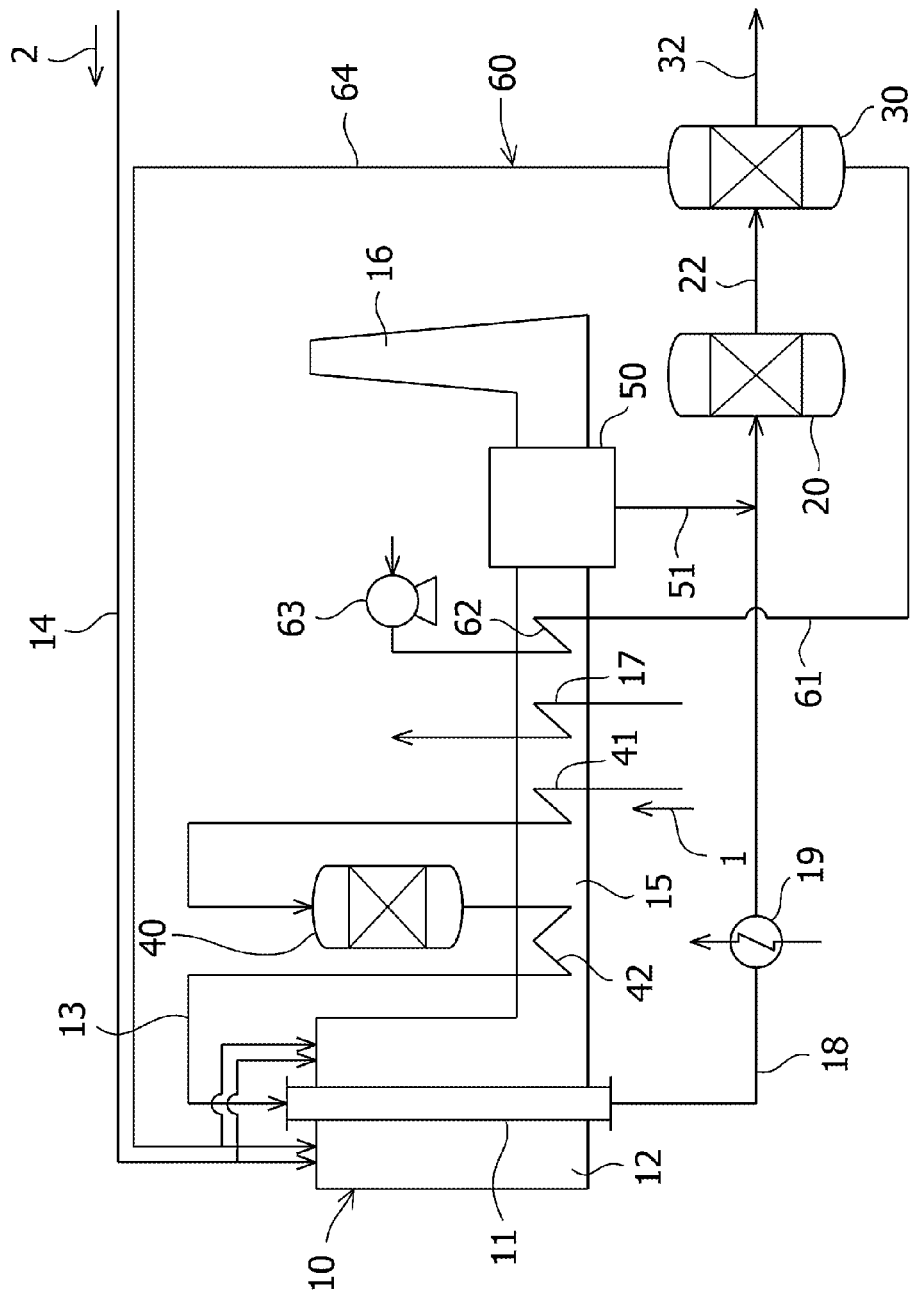
FIG. 4 is a schematic view showing an embodiment of the system for producing gasoline from natural gas via methanol according to the present invention, which is a combination of the embodiments illustrated in FIGS. 1 to 3.

Simulation of energy balance was carried out for the respective embodiments illustrated in FIGS. 1 to 3, respective embodiments including a combination of two of the embodiments illustrated in FIGS. 1 to 3, and the embodiment illustrated in FIG. 4, which includes all the embodiments illustrated in FIGS. 1 to 3. The results are shown in Table 1. Note that the simulation was carried out for the case in which the daily production of methanol was 2,500 tons. For the conditions of both the material and the fuel, natural gas was used. In addition, for comparison, results of a conventional example in which methanol is synthesized from natural gas and those of a reference example in which gasoline or DME is synthesized from natural gas via methanol are also shown in Table 1.

TABLE 1

|  |  | Conventional Example Synthesis of methanol | Reference Example 1 Synthesis of DME via methanol | Reference Example 2 Synthesis of gasoline via methanol |
|---|---|---|---|---|
| Methanol | (T/D) | 2,500 | 2,500 | 2,500 |
| DME | (T/D) | — | 1,797 | — |
| Gasoline | (barrel/D) | — | — | 8,000 |

TABLE 1-continued

| | | | | |
|---|---|---|---|---|
| LPG | (barrel/D) | — | — | 1,030 |
| Material | ($10^6$ kcal/H) | 733.5 | 733.5 | 733.5 |
| Fuel | ($10^6$ kcal/H) | 370.8 | 370.8 | 370.8 |
| Process steam | (T/H) | 211 | 211 | 211 |
| Process heat recovery | (T/H) | 176.1 | 176.1 | 176.1 |
| Flue gas heat recovery | ($10^6$ kcal/H) | 127.2 | 127.2 | 127.2 |
| Methanol synthesis heat | ($10^6$ kcal/H) | 44.4 | 44.4 | 44.4 |
| Methanol distillation heat | ($10^6$ kcal/H) | 109.5 | — | — |
| DME synthesis heat | ($10^6$ kcal/H) | — | 19.6 | — |
| MTG synthesis heat | ($10^6$ kcal/H) | — | — | 43.3 |
| $CO_2$ recovery amount | (T/H) | — | — | — |
| Heat recovered by $CO_2$ recovery | ($10^6$ kcal/H) | — | — | — |
| Heat recovered by pre-reforming | ($10^6$ kcal/H) | — | — | — |
| Heat recovered from flue gas of synthesis of MTG | ($10^6$ kcal/H) | — | — | — |
| $CO_2$ compression energy | (kw) | — | — | — |
| Auxiliary boiler | ($10^6$ kcal/H) | 18.1 | 18.1 | 18.1 |
| Residual energy | ($10^6$ kcal/H) | 0 | 129.1 | 152.8 |

| | | Example 1 Synthesis of gasoline via methanol + pre-reforming | Example 2 Synthesis of gasoline via methanol + $CO_2$ recovery | Example 3 Synthesis of gasoline via methanol + MTG heat recovery |
|---|---|---|---|---|
| Methanol | (T/D) | 2,500 | 3,375 | 2,500 |
| DME | (T/D) | — | — | — |
| Gasoline | (barrel/D) | 8,000 | 10,800 | 8,000 |
| LPG | (barrel/D) | 1,030 | 1,417 | 1,030 |
| Material | ($10^6$ kcal/H) | 733.5 | 733.5 | 733.5 |
| Fuel | ($10^6$ kcal/H) | 296.6 | 370.8 | 359.4 |
| Process steam | (T/H) | 211 | 211 | 211 |
| Process heat recovery | (T/H) | 176.1 | 176.1 | 176.1 |
| Flue gas heat recovery | ($10^6$ kcal/H) | 53.0 | 127.2 | 127.2 |
| Methanol synthesis heat | ($10^6$ kcal/H) | 44.4 | 59.9 | 44.4 |
| Methanol distillation heat | ($10^6$ kcal/H) | — | — | — |
| DME synthesis heat | ($10^6$ kcal/H) | — | — | — |
| MTG synthesis heat | ($10^6$ kcal/H) | 43.3 | 58.5 | 43.3 |
| $CO_2$ recovery amount | (T/H) | — | 1,205 | — |
| Heat recovered by $CO_2$ recovery | ($10^6$ kcal/H) | — | 32.0 | — |
| Heat recovered by pre-reforming | ($10^6$ kcal/H) | 74.2 | — | — |
| Heat recovered from flue gas of synthesis of MTG | ($10^6$ kcal/H) | — | — | 11.4 |
| $CO_2$ compression energy | (kw) | — | 7,000 | — |
| Auxiliary boiler | ($10^6$ kcal/H) | 18.1 | 0 | 18.1 |
| Residual energy | ($10^6$ kcal/H) | 60.5 | 133.4 | 123.3 |

| | | Example 4 Synthesis of gasoline via methanol + $CO_2$ recovery + pre-reforming | Example 5 Synthesis of gasoline via methanol + $CO_2$ recovery + MTG heat recovery |
|---|---|---|---|
| Methanol | (T/D) | 3,375 | 3,375 |
| DME | (T/D) | — | — |
| Gasoline | (barrel/D) | 10,800 | 10,800 |
| LPG | (barrel/D) | 1,417 | 1,417 |
| Material | ($10^6$ kcal/H) | 733.5 | 733.5 |
| Fuel | ($10^6$ kcal/H) | 296.6 | 359.4 |
| Process steam | (T/H) | 211 | 211 |
| Process heat recovery | (T/H) | 176.1 | 176.1 |
| Flue gas heat recovery | ($10^6$ kcal/H) | 53.0 | 115.8 |
| Methanol synthesis heat | ($10^6$ kcal/H) | 59.9 | 59.9 |
| Methanol distillation heat | ($10^6$ kcal/H) | — | — |
| DME synthesis heat | ($10^6$ kcal/H) | — | — |
| MTG synthesis heat | ($10^6$ kcal/H) | 58.5 | 58.5 |
| $CO_2$ recovery amount | (T/H) | 1,205 | 1,205 |
| Heat recovered by $CO_2$ recovery | ($10^6$ kcal/H) | 32.0 | 32.0 |
| Heat recovered by pre-reforming | ($10^6$ kcal/H) | 74.2 | — |
| Heat recovered from flue gas of synthesis of MTG | ($10^6$ kcal/H) | — | 11.4 |
| $CO_2$ compression energy | (kw) | 7,000 | 7,000 |
| Auxiliary boiler | ($10^6$ kcal/H) | 0 | 0 |
| Residual energy | ($10^6$ kcal/H) | 47.9 | 110.7 |

TABLE 1-continued

|  |  | Example 6<br>Synthesis of gasoline via<br>methanol +<br>pre-reforming +<br>MTG heat recovery | Example 7<br>Synthesis of gasoline via<br>methanol +<br>$CO_2$ recovery +<br>pre-reforming +<br>MTG heat recovery |
|---|---|---|---|
| Methanol | (T/D) | 2,500 | 3.375 |
| DME | (T/D) | — | — |
| Gasoline | (barrel/D) | 8,000 | 10,800 |
| LPG | (barrel/D) | 1,030 | 1,417 |
| Material | ($10^6$ kcal/H) | 733.5 | 733.5 |
| Fuel | ($10^6$ kcal/H) | 2852 | 285.2 |
| Process steam | (T/H) | 211 | 211 |
| Process heat recovery | (T/H) | 176.1 | 176.1 |
| Flue gas heat recovery | ($10^6$ kcal/H) | 53.0 | 41.6 |
| Methanol synthesis heat | ($10^6$ kcal/H) | 44.4 | 59.9 |
| Methanol distillation heat | ($10^6$ kcal/H) | — | — |
| DME synthesis heat | ($10^6$ kcal/H) | — | — |
| MTG synthesis heat | ($10^6$ kcal/H) | 43.3 | 58.5 |
| $CO_2$ recovery amount | (T/H) | — | 1,205 |
| Heat recovered by $CO_2$ recovery | ($10^6$ kcal/H) | — | 32.0 |
| Heat recovered by pre-reforming | ($10^6$ kcal/H) | 74.2 | 74.2 |
| Heat recovered from flue gas of synthesis of MTG | ($10^6$ kcal/H) | 11.4 | 11.4 |
| $CO_2$ compression energy | (kw) | — | 7,000 |
| Auxiliary boiler | ($10^6$ kcal/H) | 18.1 | 0 |
| Residual energy | ($10^6$ kcal/H) | 49.1 | 36.5 |

As shown in Table 1, in the Conventional Example for synthesizing methanol, the residual energy was 0 kcal/H for the entire system, and the self-balance was achieved. On the other hand, in the Reference Examples 1 and 2 for synthesizing DME or gasoline via methanol, the synthesis heat generated in the synthesis of DME or gasoline (MTG) increased and methanol distillation heat became unnecessary, and accordingly, excessive energy was generated.

In Example 1 in which the pre-reformer configured to carry out pre-reforming was provided, the supply of fuel and the flue gas heat recovery amount in the steam reformer decreased, and accordingly, better self-balance was achieved compared with Reference Examples 1 and 2. In addition, in Example 2 in which the $CO_2$ recovery device was provided, $CO_2$ recovery heat became necessary and the production of gasoline increased, and accordingly, better self-balance was achieved compared with Reference Examples 1 and 2. In Example 3 in which combustion air was used to recover gasoline synthesis heat (MTG heat), the supply of fuel in the steam reformer and the amount of recovered flue gas decreased, and accordingly, better self-balance was achieved compared with Reference Examples 1 and 2. Similarly in Examples 4 to 7, which are a combination of the above-described Examples, more remarkably better self-balance was achieved compared with Reference Examples 1 and 2.

DESCRIPTION OF REFERENCE NUMERALS

10: Steam reformer
11: Reaction tube
12: Burning portion
13: Material supply line
14: Fuel supply line
15: Waste heat recovery portion
16: Stack
17: Flue gas-steam heat exchanger
18: Reformed gas supply line
19: Reformed gas heat exchanger
20: Methanol synthesis column
22: Methanol supply line
30: Gasoline synthesis column
32: Gasoline supply line
40: Pre-reformer
41: First flue gas-material heat exchanger
42: Second flue gas-material heat exchanger
50: $CO_2$ recovery device
51: $CO_2$ supply line
60: Air preheater
61: Combustion air inlet line
62: Flue gas-combustion air heat exchanger
63: Fan
64: Combustion air supply line

The invention claimed is:

1. A system for producing gasoline or dimethyl ether from natural gas via methanol, comprising:
   a steam-reforming device for generating reformed gas by steam-reforming natural gas;
   a flue gas-steam heat exchanger for obtaining steam or heat to be used within the system by recovering heat from a flue gas generated in a burning portion of the steam-reforming device;
   a methanol synthesis device for synthesizing methanol from the reformed gas generated by the steam reforming device;
   a reformed gas-steam heat exchanger for obtaining steam or heat to be used within the system by recovering heat from the reformed gas which is not yet supplied to the methanol synthesis device;
   a gasoline or dimethyl ether synthesis device for synthesizing gasoline or dimethyl ether from the methanol synthesized by the methanol synthesis device; and
   a pre-reforming device for pre-reforming the natural gas prior to the steam-reforming of the natural gas;
   a first heat exchanger for preheating the natural gas which is not yet supplied to the pre-reforming device by the flue gas generated from the steam reforming device; and
   a second heat exchanger for preheating the pre-reformed natural gas discharged from the pre-reforming device by the flue gas generated from the steam reforming device, wherein an overall energy balance of the system comprising an amount of fuel supplied to the burning portion of the steam reforming device, heat recovered by the flue gas-steam heat exchanger, heat recovered by the reformed gas-steam heat exchanger, synthesis heat generated in the methanol synthesis device, synthesis heat generated in the gasoline or dimethyl ether synthesis device, and steam or heat to be used within the system is self-balanced by reducing the amount of the fuel supplied to the burning portion of the steam reforming device for the installation of the pre-reforming device to the system, and by using the synthesis heat generated in the gasoline or dimethyl ether synthesis device to compensate for a decrease in the heat recovered by the flue gas-steam heat exchanger for heat recovered by the first and second heat exchangers to the system to obtain steam or heat to be used within the system.

2. The system according to claim 1, further comprising:
a carbon dioxide recovery device for absorbing and removing carbon dioxide from flue gas of the steam reforming device by bringing $CO_2$ absorbing liquid into gas-liquid contact with the flue gas to recover carbon dioxide from the flue gas; and
a carbon dioxide supply line for supplying the recovered carbon dioxide gas from the carbon dioxide recovery device to the methanol synthesis device,
wherein the overall energy balance of the system is further self-balanced by increasing the production of methanol for the installations of the carbon dioxide recovery device and the carbon dioxide supply line to increase the synthesis heat generated in the methanol synthesis device and the synthesis heat generated in the gasoline or dimethyl ether synthesis device, and by consuming the energy for the carbon dioxide recovery device.

3. The system according to claim 1, further comprising:
a flue gas-combustion air heat exchanger for preheating combustion air to be supplied to the steam-reforming device by the flue gas generated from the steam reforming device;
a combustion air introduction line for introducing the preheated combustion air to the gasoline or dimethyl ether synthesis device; and
an air preheating device for further preheating the preheated combustion air by the synthesis heat generated from the gasoline or dimethyl ether synthesis device,
wherein the overall energy balance of the system is further self-balanced by reducing the amount of the fuel supplied to the burning portion of the steam reforming device for the installations of the air preheating device, the combustion air introduction line and the flue gas-combustion air heat exchanger, and by using the synthesis heat generated in the gasoline or dimethyl ether synthesis device to compensate for a decrease in the heat recovered by the flue gas-steam heat exchanger for heat recovered by the flue gas-combustion air heat exchanger to obtain steam or heat to be used within the system.

4. The system according to claim 2, further comprising:
a flue gas-combustion air heat exchanger for preheating combustion air to be supplied to the steam-reforming device by the flue gas generated from the steam reforming device;
a combustion air introduction line for introducing the preheated combustion air to the gasoline or dimethyl ether synthesis device; and
an air preheating device for further preheating the preheated combustion air by the synthesis heat generated from the gasoline or dimethyl ether synthesis device,
wherein the overall energy balance of the system is further self-balanced by reducing the amount of the fuel supplied to the burning portion of the steam reforming device for the installations of the air preheating device, the combustion air introduction line and the flue gas-combustion air heat exchanger, and by using the synthesis heat generated in the gasoline or dimethyl ether synthesis device to compensate for a decrease in the heat recovered by the flue gas-steam heat exchanger for heat recovered by the flue gas-combustion air heat exchanger to obtain steam or heat to be used within the system.

5. A system for producing gasoline or dimethyl ether from natural gas via methanol, comprising:
a steam-reforming device for generating reformed gas by steam-reforming natural gas;
a flue gas-steam heat exchanger for obtaining steam or heat to be used within the system by recovering heat from a flue gas generated in a burning portion of the steam-reforming device;
a methanol synthesis device for synthesizing methanol from the reformed gas generated by the steam reforming device;
a reformed gas-steam heat exchanger for obtaining steam or heat to be used within the system by recovering heat from the reformed gas which is not yet supplied to the methanol synthesis device;
a gasoline or dimethyl ether synthesis device for synthesizing gasoline or dimethyl ether from the methanol synthesized by the methanol synthesis device;
a carbon dioxide recovery device for absorbing and removing carbon dioxide from flue gas of the steam reforming device by bringing $CO_2$ absorbing liquid into gas-liquid contact with the flue gas to recover carbon dioxide from the flue gas; and
a carbon dioxide supply line for supplying the recovered carbon dioxide gas from the carbon dioxide recovery device to the methanol synthesis device, in the case of selecting the carbon dioxide recovery device,
wherein an overall energy balance of the system comprising an amount of fuel supplied to the burning portion of the steam reforming device, heat recovered by the flue gas-steam heat exchanger, heat recovered by the reformed gas-steam heat exchanger, synthesis heat generated in the methanol synthesis device, synthesis heat generated in the gasoline or dimethyl ether synthesis device, and steam or heat to be used within the system is self-balanced by increasing the production of methanol for the installations of the carbon dioxide recovery device and the carbon dioxide supply line to increase the synthesis heat generated in the methanol synthesis device and the synthesis heat generated in the gasoline or dimethyl ether synthesis device, and by consuming the energy for the carbon dioxide recovery device.

6. The system according to claim 5, further comprising:
a flue gas-combustion air heat exchanger for preheating combustion air to be supplied to the steam-reforming device by the flue gas generated from the steam reforming device;
a combustion air introduction line for introducing the preheated combustion air to the gasoline or dimethyl ether synthesis device; and
an air preheating device for further preheating the preheated combustion air by the synthesis heat generated from the gasoline or dimethyl ether synthesis device,
wherein the overall energy balance of the system is further self-balanced by reducing the amount of the fuel supplied to the burning portion of the steam reforming device for the installations of the air preheating device, the combustion air introduction line and the flue gas-combustion air heat exchanger, and by using the synthesis heat generated in the gasoline or dimethyl ether synthesis device to compensate for a decrease in the heat recovered by the flue gas-steam heat exchanger for heat recovered by the flue gas-combustion air heat exchanger to obtain steam or heat to be used within the system.

7. A system for producing gasoline or dimethyl ether from natural gas via methanol, comprising:

- a steam-reforming device for generating reformed gas by steam-reforming natural gas;
- a flue gas-steam heat exchanger for obtaining steam or heat to be used within the system by recovering heat from a flue gas generated in a burning portion of the steam-reforming device;
- a methanol synthesis device for synthesizing methanol from the reformed gas generated by the steam reforming device;
- a reformed gas-steam heat exchanger for obtaining steam or heat to be used within the system by recovering heat from the reformed gas which is not yet supplied to the methanol synthesis device;
- a gasoline or dimethyl ether synthesis device for synthesizing gasoline or dimethyl ether from the methanol synthesized by the methanol synthesis device;
- a flue gas-combustion air heat exchanger for preheating combustion air to be supplied to the steam-reforming device by the flue gas generated from the steam reforming device;
- a combustion air introduction line for introducing the preheated combustion air to the gasoline or dimethyl ether synthesis device; and
- an air preheating device for further preheating the preheated combustion air by the synthesis heat generated from the gasoline or dimethyl ether synthesis device,
- wherein an overall energy balance of the system comprising an amount of fuel supplied to the burning portion of the steam reforming device, heat recovered by the flue gas-steam heat exchanger, heat recovered by the reformed gas-steam heat exchanger, synthesis heat generated in the methanol synthesis device, synthesis heat generated in the gasoline or dimethyl ether synthesis device, and steam or heat to be used within the system is self-balanced by reducing the amount of the fuel supplied to the burning portion of the steam reforming device for the installations of the air preheating device, the combustion air introduction line and the flue gas-combustion air heat exchanger, and by using the synthesis heat generated in the gasoline or dimethyl ether synthesis device to compensate for a decrease in the heat recovered by the flue gas-steam heat exchanger for heat recovered by the flue gas-combustion air heat exchanger to obtain steam or heat to be used within the system.

* * * * *